US006365571B1

(12) United States Patent
Masuda et al.

(10) Patent No.: US 6,365,571 B1
(45) Date of Patent: Apr. 2, 2002

(54) FGF INHIBITOR, ANGIOGENESIS INHIBITOR AND ANTITUMOR AGENT CONTAINING COMPLESTATIN OR ITS DERIVATIVE AS EFFECTIVE INGREDIENT

(75) Inventors: Tsutomu Masuda; Ryohei Tsuji, both of Noda (JP)

(73) Assignee: NODA Institute for Scientific Research, Chiba-ken (JP)

( * ) Notice: Subject to any disclaimer, the term of this patent is extended or adjusted under 35 U.S.C. 154(b) by 0 days.

(21) Appl. No.: 09/296,529

(22) Filed: Apr. 22, 1999

(30) Foreign Application Priority Data

Apr. 30, 1998 (JP) .............................. 10-121178
Feb. 4, 1999 (JP) ............................ 11-026939

(51) Int. Cl.⁷ .............................................. A61K 38/00
(52) U.S. Cl. ....................................................... 514/10
(58) Field of Search ............................................. 514/10

(56) References Cited

FOREIGN PATENT DOCUMENTS

| JP | 53141201 | * 12/1978 | .................. 514/10 |
| JP | 3264535 A | 11/1991 | |
| JP | 03264535 | * 11/1991 | .................. 514/10 |
| JP | 3297390 A | 12/1991 | |
| WO | WO9922759 A1 | 5/1999 | |

OTHER PUBLICATIONS

Isao Kaneko et al., The Journal of Immunology, vol. 124, No. 3, 1980, pp. 1194–1198.
David M. Ornitz et al., Journal of Bilogical Chemistry, vol. 271, No. 25, 1996, pp. 15292–15297.
John P. Liuzzo et al., Blood, vol. 87, No. 1, 1996, pp. 245–255.
Nakoki Okada et al., Japanese Journal of Cancer Research, vol. 87, 1996, pp. 831–836.
S. Hatanaka, Molecular Medicine, vol. 30, No. 8, 1057–1058, 1993.
Fujioka et al., The Japanese Journal of Antibiotics, 41, 606, 1988.
Haruo Seto et al., Tetrahedron Letters, 30, No. 37, 4987–4950, 1989.
K. Tachikawa et al., Thrombosis and Haemostasis, vol. 77, 77, pp. 137–142 (1997).
K. Momota et al., Biochemical and Biophysical Research Communications, vol. 179, No. 1, pp. 243–250, 1991.

* cited by examiner

*Primary Examiner*—Jerome D. Goldberg
(74) *Attorney, Agent, or Firm*—Birch, Stewart, Kolasch & Birch, LLP (57) ABSTRACT

There are an FGF inhibitor, a angiogenesis inhibitor and an antitumor agent which are useful as a pharmaceutical and so forth, and comprise complestatin or its derivative as an effective ingredient.

12 Claims, 6 Drawing Sheets

Fig. 1(a)

Methanol

Fig. 1(b)

0.1N HCl/Methanol

Fig. 1(c)

0.1N NaOH/Methanol

FGF INHIBITOR, ANGIOGENESIS INHIBITOR AND ANTITUMOR AGENT CONTAINING COMPLESTATIN OR ITS DERIVATIVE AS EFFECTIVE INGREDIENT

BACKGROUND OF THE INVENTION

1. Field of the invention

The present invention relates to an FGF inhibitor, angiogenesis inhibitor and antitumor agent containing complestatin or its derivative as an effective ingredient.

2. Prior Art

Although angiogenesis is a biological phenomenon essential for prefetal formation of the vascular system and organ morphogenesis as well as growth and development of the vascular system accompanying body growth, following the onset of puberty, angiogenesis is not observed in mature individuals with the exception of transient angiogenesis accompanying estrus and pregnancy in women.

On the other hand, pathological increases in vascularization are related to the onset and progress of numerous diseases, including various types of inflammatory diseases (rheumatism, psoriasis), diabetic retinopathy and cancer. The proliferation and metastasis of solid tumors in particular are believed to be intimately involved with angiogenesis.

The first step of angiogenesis is thought to begin with binding by various cell growth factors and so forth to receptors on the surface of vascular endothelial cells resulting in promotion of proliferation and migration of vascular endothelial cells. Fibroblast growth factor (FGF) has been shown to function as a angiogenesis factor in both in vivo and in vitro model experimental systems, and is considered to be one of the angiogenesis factors in pathological states.

On the other hand, binding of cell growth factor to receptors on the surface of cancer cells is considered to be necessary for spontaneous cell proliferation and tumor formation. For example, FGF is known to be produced excessively in many gliomas, and FGF receptors are known to appear. Thus, it is believed that an autocrine mechanism in which FGF produced by the tumor itself stimulates the same tumor functions in the formation of gliomas and other tumors.

Although extremely small amounts of basic fibroblast growth factor (bFGF), a type of FGF, appear at normal sites of the brain, abnormal expression of bFGF is observed in nearly all brain tumors, and receptors for bFGF are present on brain tumor cells. Moreover, it is known in animal experiments that progression of brain tumors is inhibited by an antibody against bFGF. Based on these findings, tumor cells in brain tumors are thought to proliferate by an autocrine mechanism. In cases other than brain tumors as well, blood bFGF levels are known to be remarkably increased in patients with lung cancer, kidney cancer and so forth, and bFGF is believed to be functioning as an autocrine signal of tumor proliferation (see Shoichi Hatanaka, Molecular Medicine, 30, 1057, 1993).

Based on the above, FGF inhibitors are expected to serve as angiogenesis inhibitors and antitumor agents for the prevention, treatment and amelioration of various diseases, as well as research reagents and so forth. Several reports have been published relating to FGF inhibitory substances in the past, but effective substances able to withstand practical use have not yet to be found.

SUMMARY OF THE INVENTION

An object of the present invention is to provide an FGF inhibitor, angiogenesis inhibitor and antitumor agent that are useful as pharmaceuticals, etc.

In consideration of the above-mentioned present circumstances, the inventors of the present invention searched for an FGF inhibitory substance having more potent inhibitory activity using a microbial culture broth as the raw material. As a result, they found that microorganisms belonging to the genus Streptomyces produced an FGF inhibitory substance, that said FGF inhibitory substance is complestatin, and that complestatin is useful as an FGF inhibitor, angiogenesis inhibitor and antitumor agent, thereby leading to completion of the present invention.

Namely, the present invention relates to an FGF inhibitor, angiogenesis inhibitor and antitumor agent containing complestatin or its derivative as an effective ingredient. In addition, the present invention also relates to a process for producing complestatin.

BRIEF DESCRIPTION OF THE DRAWINGS

FIG. 1(*a*) to 1(*c*) are graphs showing the ultraviolet absorption spectra in each solution of the FGF inhibiting substance (complestatin) obtained in Example 2.

DESCRIPTION OF THE PREFERRED EMBODIMENTS

1. Complestatin and its Derivatives

Complestatin is a compound that was isolated and structurally identified as an anti-complement substance from a culture broth of *Streptomyces lavendulae* (Fujioka, et al., Jpn. J. Antibiotics, 41, 606, 1988), and it has been disclosed in Japanese Patent Laid-Open Publications Nos. 53-141201 and 3-264535 that it exhibits inhibitory action of complement activity, and anti-human immunodeficiency virus action, respectively. In addition, it has also been reported to promote thrombolysis (Tachikawa, K. et al., Thromb. Haemost., 77, 137, 1997). However, it is not described in said specifications or in said report that complestatin has FGF inhibitory action, angiogenesis inhibitory action or antitumor action. The structural formula of complestatin is shown below.

In the above-mentioned structural formula, various optical isomers are all indicated with a single formula. Thus, these optical isomers and their mixtures are all included in the complestatin referred to in the present invention.

Complestatin derivatives refer to compounds in which a portion of the structure of complestatin has been altered or modified, and there are no particular restrictions on these derivatives provided that they have either of FGF inhibitory activity, angiogenesis inhibitory activity or antitumor activity. Examples of said derivatives include pharmacologically acceptable salts, esters or prodrugs and so forth of complestatin.

Pharmacologically acceptable salts of complestatin is not particularly limited, and examples of which include salts of alkali metals (e.g., sodium and potassium), alkaline earth metals (e.g., magnesium and calcium), and their hydroxides or carbonates and alkali metal alkoxides (e.g., sodium methoxide and potassium-t-butoxide). In addition, examples of salts include acid addition salts formed by addition of inorganic acids (e.g., hydrochloric acid, sulfuric acid and phosphoric acid) or organic acids (e.g., maleic acid, citric acid, fumaric acid and p-toluene-sulfonic acid), as well as addition salts of amines and addition salts of amino acids. Furthermore, hydrates of the above-mentioned salts are also included in the salts referred to here.

There are no particular restrictions on esters of complestatin provided they are esters produced in an esterification reaction with alcohol or carboxylic acid. Examples of alcohols include an aliphatic alcohol having 1 to 4 carbon atoms such as methanol, ethanol, 1-propanol and 2-propanol, while examples of carboxylic acids include an organic carboxylic acid having 1 to 4 carbon atoms such as formic acid, acetic acid and lactic acid.

Prodrugs of complestatin refer to compounds that express FGF inhibitory action, angiogenesis inhibitory action or antitumor action by changing into complestatin after it has been administered to the body. Complestatin having been converted to a prodrug for the purpose of improved stability and absorptivity or reduction of adverse side-effects are included in the derivatives of complestatin referred to in the present invention.

2. Process for Producing Complestatin or its Derivative

Complestatin or its derivatives (to be generically referred to as complestatins) may be produced by any method, and examples of methods that are widely used include methods involving collection and purification from microbial culture liquids, chemical synthesis methods and semi-synthesis methods.

For example, complestatin can be collected and purified from a culture of microorganisms that produce complestatin. In addition, pharmacologically acceptable salts of complestatin can be produced by allowing an alkali metal, alkaline earth metal, alkali metal alkoxide, inorganic acid or organic acid to act on complestatin collected and purified from a culture of microorganism. Moreover, esters of complestatin can be produced by allowing an alcohol or carboxylic acid to act on complestatin in the presence of an acid catalyst.

In the following, a method for collecting and purifying complestatin from a culture of microorganism is explained.

Any microbial strains that produces complestatin can be used for the microorganism. Examples of such microorganisms include those belonging to the genus Streptomyces such as Streptomyces lavendulae SANK60477, Streptomyces sp. WK-3419, and Streptomyces sp. A1631 (Japanese Patent Laid-Open Publication No. 53-141201; Tanaka, H. et al., J. Antibiotics, 50, 58, 1997; Tachikawa, K. et al., Thromb. Haemost., 77, 137, 1997). Particularly preferable examples of microbial strains include Streptomyces sp. No. 989 (FERM BP-6331 deposited on Apr. 27, 1998 at National Institute of Bioscience and Human-Technology, Agency of Industrial Science and Technology) isolated from soil in Akita prefecture, Japan by the inventors of the present invention. Complestatin is obtained by culturing microorganisms producing complestatin under normally suitable culturing conditions followed by the addition of organic solvent (such as ethyl acetate, acetone or their mixed solvents) to the culture, extraction of the contents of the cultured cells is carried out. Then, complestatin contained in said contents is purified in view of FGF inhibitory activity as an index. Examples of purification methods that can be used include solvent extraction using water, an organic solvent or their mixed solvents, various types of chromatography, recrystallization from a single solvent or mixed solvent and other routine methods, either alone or in combination as is suitable. In addition, freeze-drying processing may be performed if necessary. As a result of the above, highly purified complestatin can be obtained.

In the case of isolating microorganisms producing complestatin from the soil and so forth, the production of FGF inhibiting substance by the detected microorganism should be used as the indicator. In this case, the method of A. Yayon, et al. (Proc. Natl. Acad. Sci. USA, 90, 10643, 1993) can be used. This method uses inhibition of binding of FGF labeled with a radioisotope to specific receptors expressed on the cell surface as the indicator. In addition, the method of A. Yayon, et al. can also be used in the case of measuring the FGF inhibitory activity of fractions obtained at each stage of collecting and purification of complestatin.

Structural analysis of purified complestatin can be performed by routine methods including elementary analysis, mass analysis, nuclear magnetic resonance analysis (NMR) and melting point measurement.

3. Agents Containing Complestatins as an Active Ingredient (1) FGF Inhibitors Containing Complestatins as an Active Ingredient As indicated in Example 3, complestatin has excellent FGF inhibitory activity. Thus, FGF inhibitors containing complestatins as an active ingredient are useful as drugs for the prevention, treatment and amelioration of diseases in which it is effective to inhibit FGF. Examples of such diseases include diseases accompanying vascularization caused by FGF stimulation, tumors accompanying cell growth caused by FGF stimulation, and tumors accompanying abnormal expression of FGF (e.g., brain tumors, lung cancer and kidney cancer).

In addition, the FGF inhibitor of the present invention is also useful as a reagent for research on FGF and on diseases in which it is effective to inhibit FGF.

(2) Angiogenesis Inhibitors Containing Complestatins as an Active Ingredient

As shown in Example 4, complestatin has excellent vascularization inhibitory activity. Thus, angiogenesis inhibitors containing complestatins as an active ingredient are useful as drugs for the prevention, treatment and amelioration of diseases in which it is effective to inhibit angiogenesis. Examples of such diseases include various diseases accompanying angiogenesis, specific examples of which include inflammatory diseases (e.g., rheumatism, rheumatoid arthritis and psoriasis), atherosclerosis, diabetic retinopathy and various solid tumors (e.g., stomach cancer, colon cancer, lung cancer and pancreas cancer).

In addition, the angiogenesis inhibitor of the present invention is also useful as a reagent for research on angiogenesis and diseases in which it is effective to inhibit angiogenesis.

Furthermore, the angiogenesis inhibitor of the present invention can also be used as an inhibitor of vascularization not involving FGF, and is useful as a drug for the prevention, treatment and ameliorization of various diseases involving angiogenesis or as a reagent for research on said diseases.

(3) Antitumor Agents Containing Complestatins as an Active Ingredient

As shown in Example 5, complestatin has excellent antitumor activity. Thus, antitumor drugs containing complestatins as an active ingredient are extremely useful both medically and in terms of scientific research.

The antitumor agent of the present invention is extremely useful as a drug for the prevention, treatment and ameliorization of not only tumors involving FGF or solid tumors involving angiogenesis (e.g., stomach cancer, colon cancer, lung cancer and pancreas cancer), but also of other tumors not involving FGF or angiogenesis, as well as a reagent for research on said tumors. Examples of tumors not involving angiogenesis include cancer of the blood and ascites cancer.

4. Usage Method of Agents Containing Complestatins as an Active Ingredient

Agents containing complestatins as an active ingredient can be used as pharmaceuticals, over-the-counter medications, research reagents and so forth either in their original form or in the form of a composition containing other ingredients. In addition, the above-mentioned agents can be used by adding to cosmetics such as externally applied skin agents and bathing agents as well as foods and beverages.

The complestatins used in the present invention may be highly purified according to the previously described methods, or may in a crude form. When complestatins originate in microorganisms, the crude product refers to a culture of the microorganisms, a culture following lysis of microorganism cells, or a fraction containing complestatins obtained at each stage of purification.

The other ingredients referred to above are not particularly limited, and examples include compounds that have FGF inhibitory activity, vascularization inhibitory activity or antitumor activity other than complestatins. In addition, other ingredients refer to, for example, pH adjusting agents, vehicles, colorants, flavorings and scents that are routinely used during preparation of pharmaceuticals, over-the-counter medications and research reagents.

The following indicates examples of usage methods for FGF inhibitors, angiogenesis inhibitors and antitumor agents containing complestatins as an active ingredient. Furthermore, the usage methods of the above-mentioned preparations are not limited to those indicated, but rather other usage methods can also be used.

(1) Usage Methods as Pharmaceuticals or Over-the-counter Medications

In the case of using complestatins as a pharmaceutical or over-the-counter medication for prevention, treatment or amelioration of various diseases, they may be administered orally in the form of tablets, powders, granules, capsules, syrup and so forth. In addition, they may also be administered parenterally in the form of sprays, suppositories, injections, external agents, intravenous drips and so forth. Although the dosage varies considerably according to the degree of the symptoms, age, disease type and so forth, they can be administered at 10 mg or more per day, and preferably 50–1000 mg per day as the normal adult dosage.

When preparing complestatins in the form of a preparation, they are manufactured according to routine methods using ordinary preparation carriers. Namely, in the case of preparing a solid oral preparation, after adding a vehicle and, if necessary, binder, disintegrating agent, lubricant, colorant, flavoring, scent and so forth to the primary drug, the preparation is formed into tablets, coated tablets, granules, powders, capsules and so forth in accordance with routine methods. These tablets and granules may be coated with a sugar coating, gelatin coating and so forth.

In the case of preparing an injection preparation, pH adjusting agent, buffer, stabilizer, solubilizer and so forth are added to the complestatins, the primary drug, followed by the preparation of an injection preparation for subcutaneous, intramuscular or intravenous injection in accordance with routine methods.

(2) Usage Methods as Research Reagents

In the case of using complestatins as research reagents, there are no particular restrictions on the form of said reagents or on the ingredients other than complestatins contained in the reagents. The form of the reagents may be a solution, powder or granules. In the case of preparing the reagent in the form of a liquid, complestatins should be dissolved in a suitable solution (for example, distilled water, physiological saline, phosphate buffer, Tris buffer, Tricine (n-Tris(hydroxymethyl)methyl glycine) buffer or sodium acetate buffer).

Examples of the ingredients other than complestatins include osmotic pressure regulators, pH adjusting agents, and substances involved in improving the storage properties of the reagent, specific examples of which include sucrose, N-2-hydroxyethylpiperazine-N'-3-propanesulfonic acid (HEPES), Tricine, Tris buffer, ethylenediaminetetraacetic acid disodium salt (EDTA-2Na), dithiothreitol (DTT), ammonium sulfate and 2-mercaptoethanol.

(3) Usage Methods in the Case of Adding to Cosmetics, Foods or Beverages

In the case of using complestatins as a drug for the prevention, treatment or amelioration of various diseases, complestatins may be used by adding to cosmetics, foods or beverages.

The cosmetics are not particularly limited, and examples of such include externally applied skin agents and bathing agents. Other normally used ingredients such as oils, alcohols, perfumes, water, thickeners and colorants can be suitably blended into these cosmetics. In addition, the foods and beverages are not particularly limited, and examples of these include edible powders, processed vegetables, processed marine products, seasonings, confections, breads, soft drinks, fruit juices, vegetable juices, dairy products and liquors.

The amount of complestatins added to cosmetics, foods or beverages should be suitably determined according to the type of target disease, and the status of the patient who is to use or consume the cosmetics, foods or beverages.

EXAMPLES

The present invention is described in detail according to the following examples, and the present invention is not limited to these examples.

Example 1

Isolation and identification of microorganisms producing FGF inhibitory substance 1. Isolation of Microorganisms Producing FGF Inhibitory Substance Microorganisms that produce FGF inhibitory substance were isolated from the soil according to the method described below.

(1) After drying soil collected in Akita prefecture, Japan, the soil was suitably diluted by adding physiological saline. Next, after mixing 1 ml of diluted soil solution and 15 ml of isolation medium warmed to 55° C. (1 g of humic acid, 0.5 g of dipotassium phosphate, 1 g of vitamin for minimum essential medium Eagle (MEM) (available from Nissui Seiyaku Co.), 25 mg of cycloheximide (available from Sigma Co.), 15 g of agar and 1 liter of tap water (pH 7.2)), the mixture was inoculated onto a plate and cultured for 7 days at 28° C.

(2) One loopful of multiple colonies that appeared was respectively inoculated in large test tubes each containing 5 ml of C4 medium (prepared by mixing 0.1% beef extract, 2% glucose, 0.2% sodium chloride, 0.005% dipotassium phosphate, 1% starch (soluble), 0.4% dry yeast and 2.5% soybean meal followed by adjusting a pH to 7.2 with 4N sodium hydroxide), and cultured for 5 days at 30° C. Two volumes of acetone were added to the culture and extracted overnight at 4° C., and the resulting supernatant was used as the sample solution.

(3) Inhibitory effects on binding of bFGF to receptors was investigated for the above-mentioned sample solution according to the method of A. Yayon, et al. (Proc. Natl. Acad. Sci., USA, 90, 10643, 1993).

Namely, 1 ml of medium containing mouse fibroblast cell Balb/3T3 clone A31 cells at a concentration of $1 \times 10^5$ cells/ml (Dulbecco's modified Eagle's medium containing 10% calf serum, 25 mM HEPES (pH 7.5), 10 units/ml of penicillin and 10 µg/ml of streptomycin (10% CS/DMEM)) was added to a 24-well culture plate, and cultured for one day at 37° C. in a $CO_2$ incubator. Furthermore, mouse fibroblast cells are known to express FGF receptors on their cell surfaces (J. Biol. Chem., 268, 9611, 1993).

After culturing, the plate was pre-cooled in a refrigerator for 2 hours. All of the following procedures were performed while cooling with ice, and the media and buffers used were all cooled prior to use. After discarding the medium and washing twice with DMEM (binding medium) containing 0.1% bovine serum albumin (BSA), 0.35 ml of binding medium containing 10 µl of the sample solution and 2 ng/ml of $^{125}$I-labeled bFGF (available from NEN Co.) were added to the plate followed by incubation for 1.5 hours at 4° C. The above procedure was used to bond bFGF to cell surface receptors.

Following completion of the reaction, after removing the binding medium and washing once with cold binding medium, the plate was washed twice with cold PBS (0.2 g potassium chloride, 0.2 g potassium primary phosphate, 8 g sodium chloride, 1.15 g sodium secondary phosphate and 1 liter of deionized water) at pH 7.5 containing 1.6 M sodium chloride. Next, 0.5 ml of 20 mM sodium acetate solution at pH 4.0 containing 2 M brine were added to the solution and receptor-bound $^{125}$I-bFGF was recovered. This procedure was repeated again, the solution was combined with the previous solution and then transferred to an RIA tube where radioactivity was measured with a gamma counter (available from Pharmacia Co.).

The amount of bFGF bound to receptors (specifically bound amount) was determined according to the following formula:

Specifically bound amount=Total bound amount−non-specifically bound amount

Furthermore, radioactivity in the case of not adding the sample solution to the binding medium was taken to represent the total bound amount, while radioactivity in the case of adding non-labeled bFGF (available from R&D Systems Co.) at 1000 times the amount of $^{125}$I-bFGF was taken to represent the non-specifically bound amount.

(4) As a result of the above, strain No. 989 was selected as a microbial strain that produces a substance that inhibits binding of bFGF to receptors, namely FGF inhibiting substance.

2. Identification of Microbial Strain No. 989 Producing FGF Inhibiting Substance Strain No. 989 is present in both innate mycelia and aerial mycelia, and although it does not form verticillate branches, flagellated spores or sporangia, it does form numerous spiral chain spores in aerial mycelia. It grows best at a growth temperature of 30° C., and does not grow at 35° C.

Moreover, since this microbial strain has LL-DAP (LL-diaminopimelic acid) in its cell wall, it was thought to belong to the genus Nocardioides, Kineosporia, Sporichthya or Streptomyces. In addition, since its menaquinone type is MK-9(H6) and (H8), it was determined to belong to either the genus Sporichthya or Streptomyces. Since innate mycelia are not present in actinomyqetes of Sporichthya species, and growth (22–42° C.) is typically weak, it is different from this microbial strains.

Since the above-mentioned test results coincide with the characteristics of Streptomyces species, this microbial strains was identified as an actinomycete of the genus Streptomyces, and was named Streptomyces sp. No. 989. Streptomyces sp. No. 989 has been deposited on Apr. 27, 1998 as FERM BP-6331 at the National Institute of Bioscience and Human-Technology, Agency of Industrial Science and Technology.

Example 2

Purification and Structural Analysis of FGF Inhibiting Substance

FGF inhibiting substance was collected and purified from a culture of Streptomyces sp. No. 989 according to the method described below, and its structure was analyzed.

Furthermore, the FGF inhibitory activity of fractions obtained at each stage of purification was investigated according to the method of A. Yayon, et al. (Proc. Natl. Acad. Sci. USA, 90, 10643, 1993) used in Example 1, section (3).

1. Purification of FGF Inhibiting Substance (1) One loopful each of a slant culture of Streptomyces sp. No. 989 was inoculated into six large test tubes containing 10 ml of modified C4 medium (prepared by mixing 0.1% beef extract, 2% glucose, 0.2% sodium chloride, 0.005% dipotassium phosphate, 1% starch (soluble), 0.4% dry yeast, 1% polypeptone and 2% celite followed by adjusting the pH to 7.2 with 4 N sodium hydroxide), and cultured for 3 days at 30° C. Next, 20 ml aliquots of this culture were added to two jar fermenters having a volume of 3 liters containing 1.5 liters of modified C4 medium followed by culturing for 5 days (ventilation level: 1 vvM, rotating speed: 350 rpm, temperature: 28° C.).

(2) After completion of culturing, adding 6 liters of acetone and extracting overnight at 4° C., a filtration aid was added followed by filtration to obtain 8 liters of extract. This extract liquid was concentrated under reduced pressure to obtain 2 liters of aqueous solution. This aqueous solution was adsorbed onto 600 ml of HP-20 resin (trade name, available from Mitsubishi Chemical Co.) and after washing with 1.8 liters of deionized water, the adsorbed fraction was eluted with 1.8 liters of 80% methanol. This eluate was concentrated under reduced pressure to make the amount 400 ml followed by adjusting the pH to 2.5 with 9 N hydrochloric acid and addition of 400 ml of ethyl acetate followed by stirring to obtain an ethyl acetate layer. Moreover, this procedure was repeated twice and the resulting ethyl acetate layers were combined with the previously obtained ethyl acetate layer followed by evaporation to dryness under reduced pressure to obtain 630 mg of a dried product.

(3) This dried product was sprinkled onto 20 ml of YMC-ODS gel (trade name, available from YMC Co.) and applied to 200 ml of an ODS column packed with 40% acetonitrile solution containing 0.1% trifluoroacetate (TFA). After washing the column with 1 liter of 40% acetonitrile solution containing 0.1% TFA, the adsorbed fraction was eluted using 45% acetonitrile containing 0.1% TFA. The fraction having FGF inhibitory activity (200 ml) was immediately neutralized with 1 N aqueous sodium hydroxide solution.

(4) The neutralized eluate was concentrated under reduced pressure and after reducing to a volume of 100 ml, it was adsorbed to 40 ml of HP-20SS resin (Mitsubishi Chemical). After washing with 120 ml of deionized water, the adsorbed fraction was eluted with 120 ml of 80% methanol. After evaporating this eluate to dryness under reduced pressure, it was dissolved in 20 ml of deionized water and freeze-dried to obtain 120 mg of a yellow crystalline powder.

2. Structural analysis of FGF inhibiting substance

The physicochemical properties of the yellow crystalline powder obtained above, namely FGF inhibiting substance, were measured for the parameters indicated below. In addition, each measurement chart is shown in FIGS. 1 through 4.

(1) Measurement of Melting Point

Melting point was measured by using the micro melting point apparatus model MP-S2 (available from Yanagimoto Seisakusho Co.).

(2) Molecular Weight

Molecular weight was measured by mass spectrometry (FAB mass spectrum). Instrument used: JMS HX-100 (available from Nihon Denshi Co.).

(3) Elementary Analysis

Organic elementary analysis was by performed using the Model CHN-Corder MT-3 (trade name, available from Yanagimoto Seisakusho Co.).

(4) Specific Rotation

Specific rotation was measured by using the SEPA-300 (trade name, available from Horiba Co.).

(5) Ultraviolet Absorption Spectrum

Ultraviolet absorption spectrum was measured by using the three types of solvents indicated below. Instrument used: U-3000 (trade name, available from Hitachi, Ltd.)

Figure 1A:
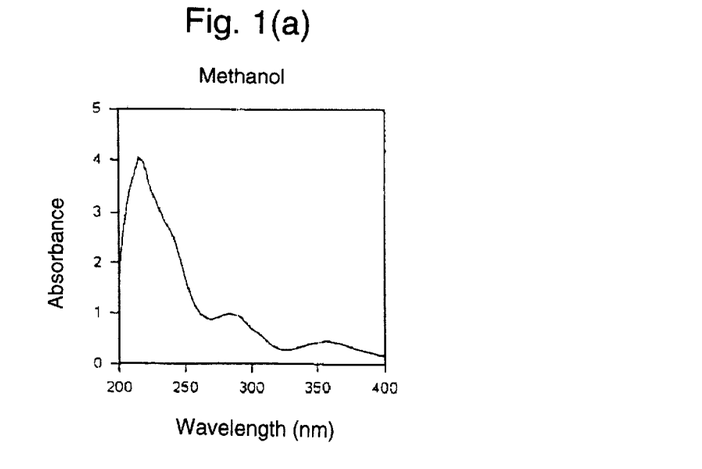

(a) Methanol (FIG. 1(a))

Figure 1B:
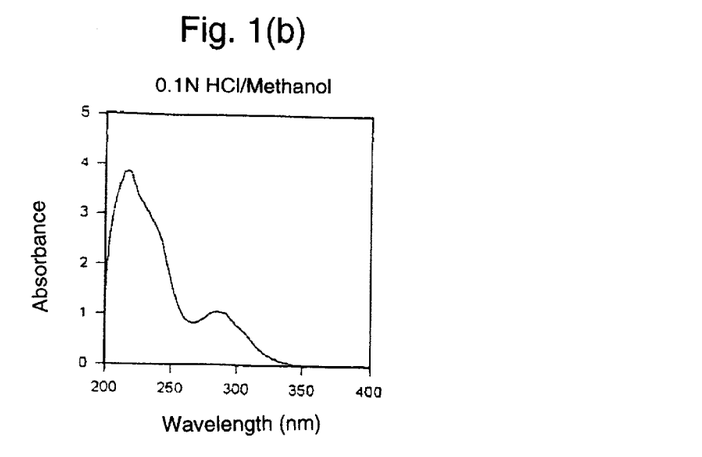

(b) Methanol containing 0.1 N hydrochloric acid (FIG. 1(b))

Figure 1C:
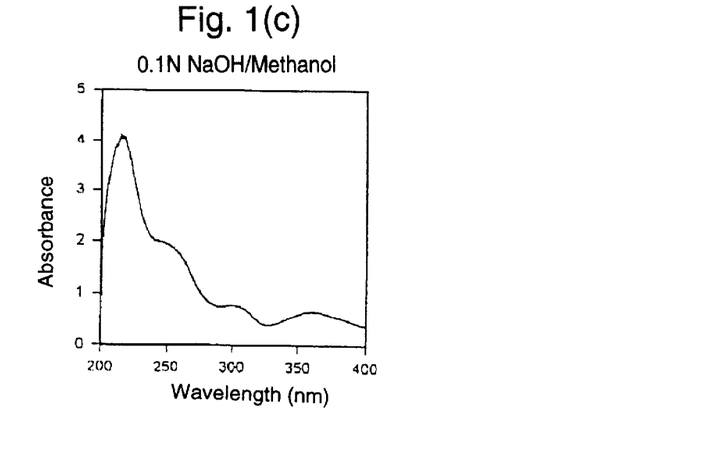

(c) Methanol containing 0.1 N sodium hydroxide (FIG. 1(c))

(6) Infrared Absorption Spectrum

Figure 2:
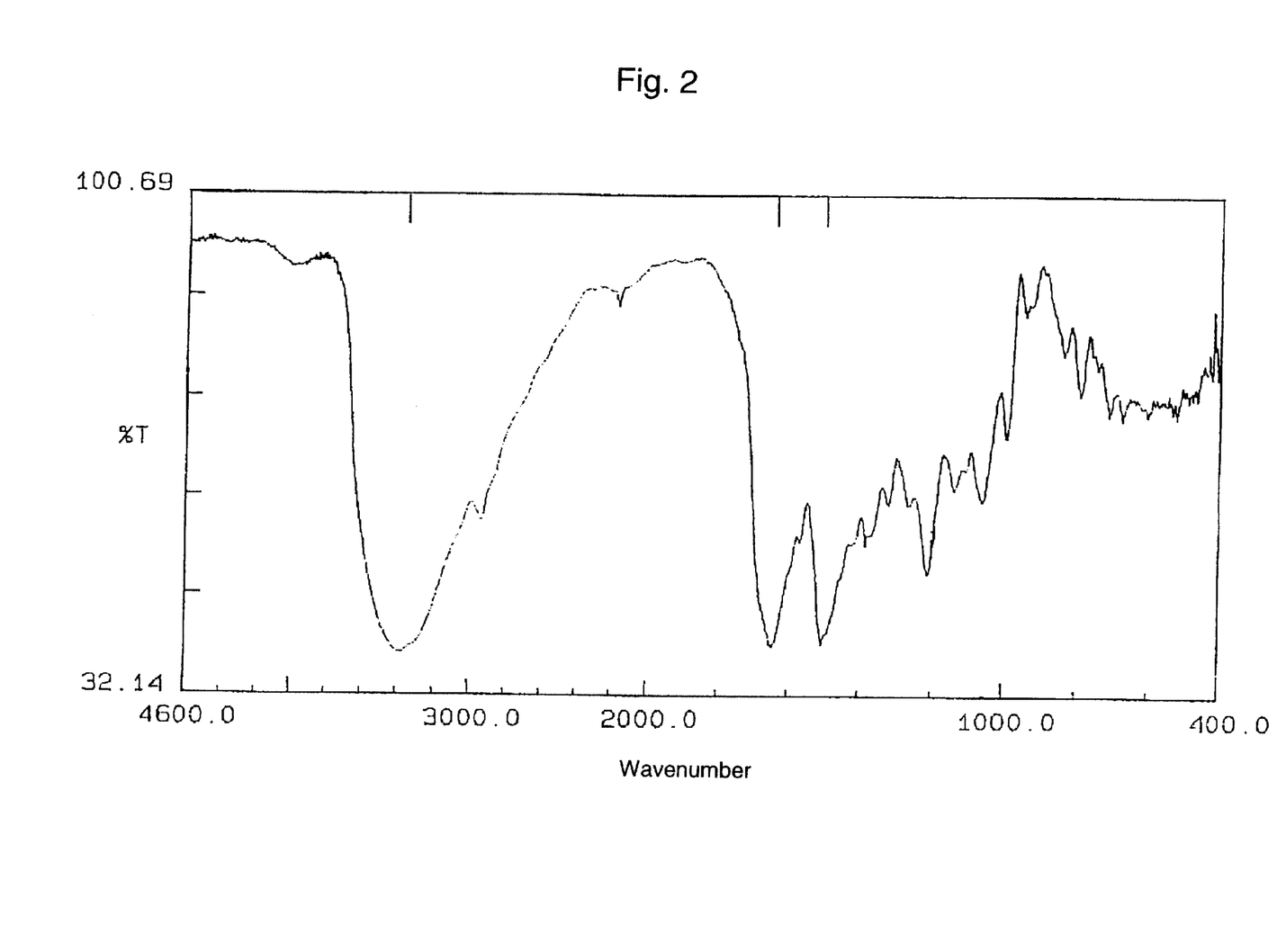
FIG. 2 is a graph showing the infrared absorption spectrum of the FGF inhibiting substance (complestatin) obtained in Example 2.

Infrared absorption spectrum was measured by mixing FGF inhibiting substance and potassium bromide. Instrument used: FT/IR-7300 (trade name, available from Nihon Bunko Kogyo Co.) (FIG. 2).

(7) $^{13}$C Nuclear Magnetic Resonance Spectrum ($^{13}$C-NMR)

Figure 3:
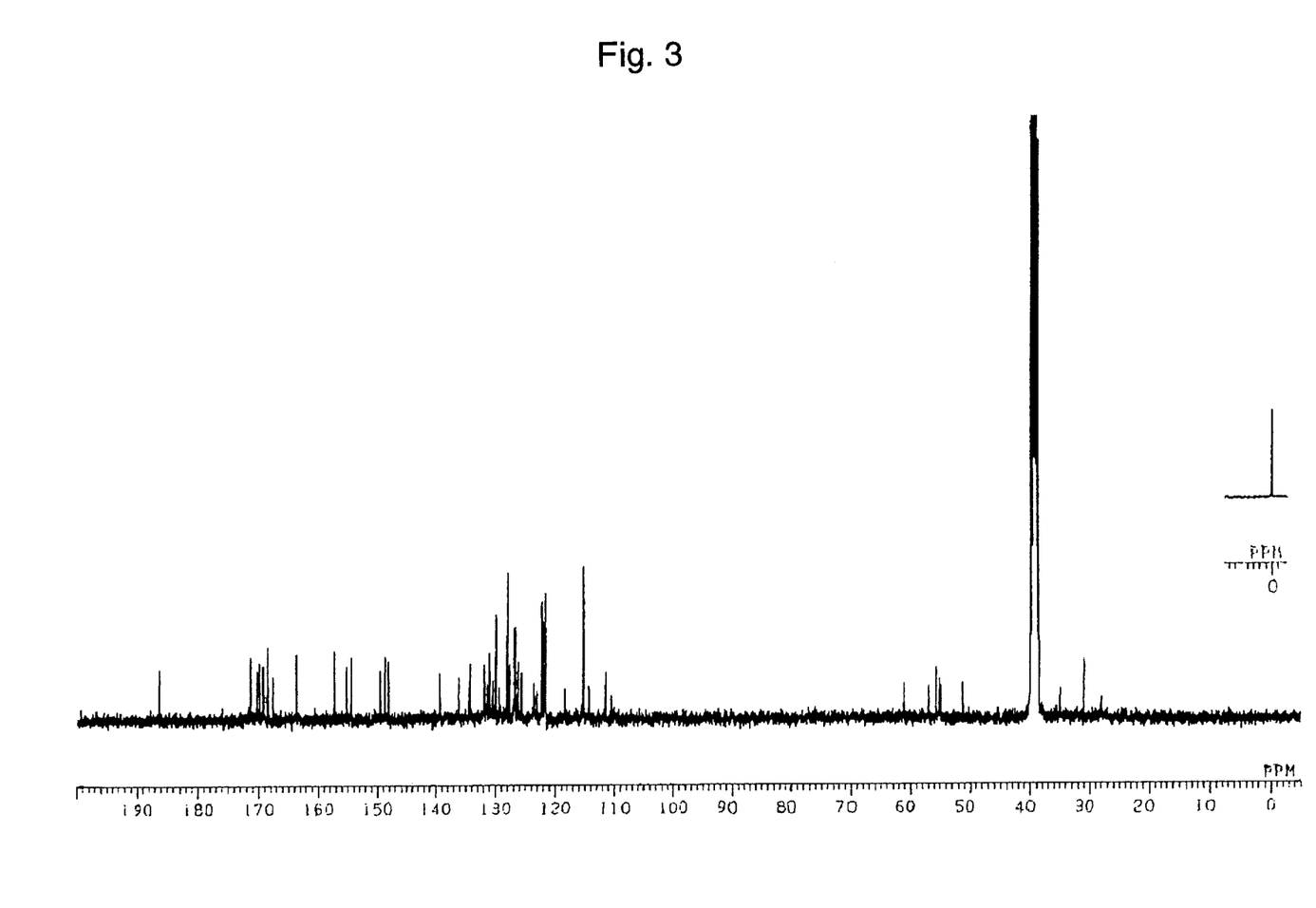
FIG. 3 is a graph showing the $^{13}$C nuclear magnetic resonance spectrum of the FGF inhibiting substance (complestatin) obtained in Example 2.

$^{13}$C-NMR was measured by using dimethylsulfoxide (DMSO) converted into an acidic state using a hydrochloric acid gas for the solvent, and using tetramethylsilane (TMS) for the external standard. Instrument used: JNM GX-400 FT (trade name, available from Nihon Denshi Co.) (FIG. 3).

(8) $^{1}$H Nuclear Magnetic Resonance Spectrum ($^{1}$H-NMR)

Figure 4:
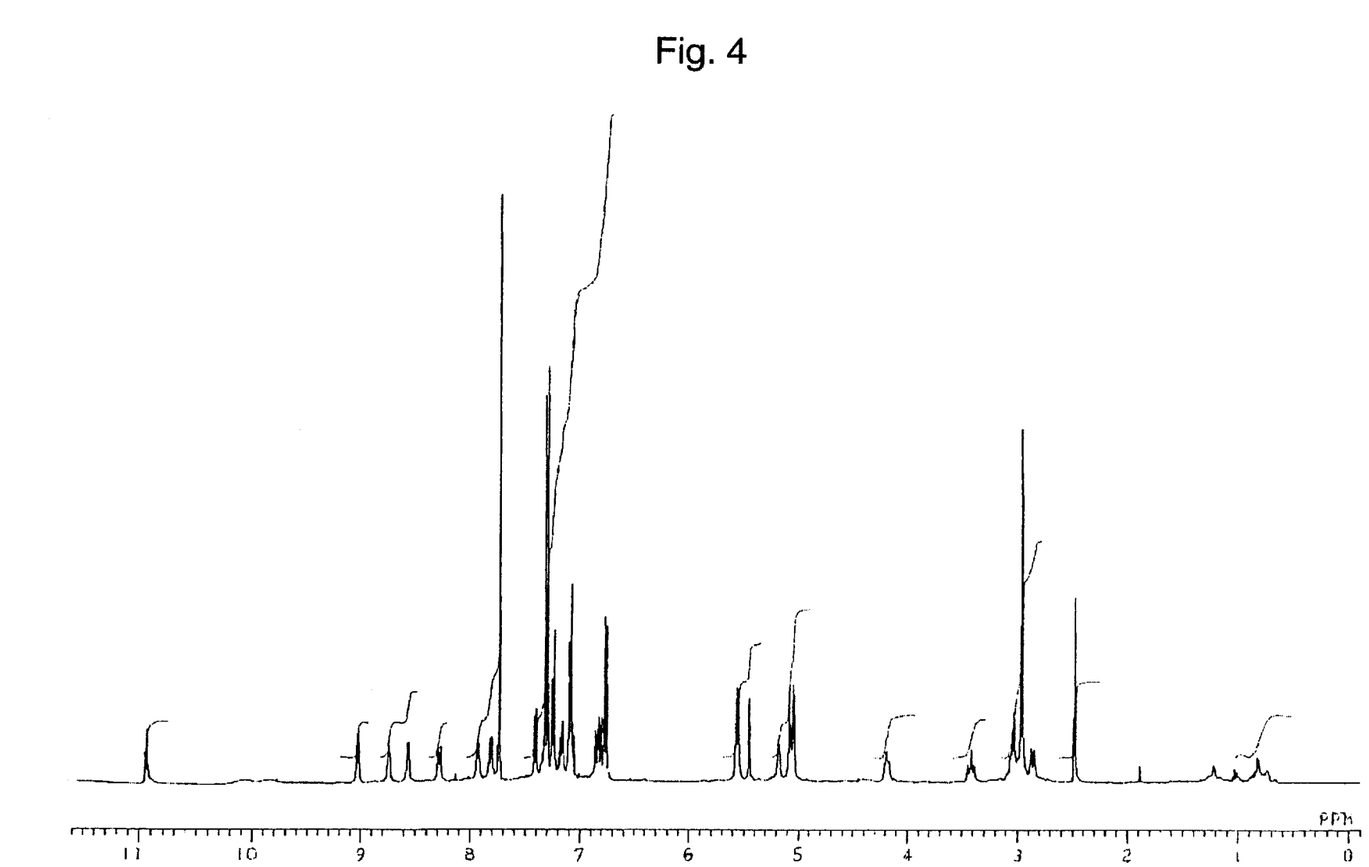
FIG. 4 is a graph showing the $^{1}$H nuclear magnetic resonance spectrum of the FGF inhibiting substance (complestatin) obtained in Example 2.

$^{1}$H-NMR was measured by using dimethylsulfoxide (DMSO) converted into an acidic state using a hydrochloric acid gas for the solvent, and using tetramethylsilane (TMS) for the external standard. Instrument used: JNM GX-400 FT (trade name, available from Nihon Denshi Co.) (FIG. 4).

The results of the above-mentioned measurements were compared with the physicochemical properties of complestatin described in J. Antibiotics, 42, 236, 1989 (Reference 1) and Tetrahedron Letters, 30, 4987, 1989 (Reference 2), on the basis of which the FGF inhibiting substance purified in the above manner was judged to be complestatin.

The physicochemical properties of the purified FGF inhibiting substance and complestatin described in each of the references are shown in Table 1. In addition, the values of the chemical shifts of the $^{1}$H-NMR spectrum are shown in Table 2, while the values of the chemical shifts of the $^{13}$C-NMR spectrum are shown in Table 3.

TABLE 1

| | Physicochemical properties of FGF inhibiting substance | Physicochemical properties of complestatin described in Reference 1 |
|---|---|---|
| Shape | Yellowish powder | Yellowish powder |
| Melting point | >270° C. (decomp.) | >300° C. (decomp.) |
| Mass spectrum FAB Mass (positive) | m/z 1326 (MH$^+$) | m/z 1325 (MH$^+$) |
| Molecular weight | 1325 | 1325 |
| Elemental analysis value | C: 53.99% H: 3.66% N: 6.95% | C: 54.13% H: 3.81% N: 7.27% Cl: 15.45% |
| Specific rotatory power [α]$_D$ | +27.3° (c 0.12, MeOH- 0.01N NaOH = 2:1) | +24.50° (c 0.13, MeOH- 0.01N NaOH = 2:1) |
| Ultraviolet rays absorption spectrum Solvent: methanol | 210, 240, 280, 290, 356 | 282, 292 |
| Solvent: Methanol containing 0.1N Hydrochloric acid | 230(sh), 280, 302 | 282, 292 |

TABLE 1-continued

| | Physicochemical properties of FGF inhibiting substance | Physicochemical properties of complestatin described in Reference 1 |
|---|---|---|
| Solvent: Methanol containing 0.1N sodium hydroxide | 220, 245, 300, 360 | 292, 355 |
| Infrared absorption spectrum IR $\upsilon_{max}$ (KBr, cm$^{-1}$) | 3360, 2930, 1640, 1510, 1380, 1320, 1260, 1210, 1140, 1060, 1000, 950, 790 | 3400, 1650, 1510, 1490 |

TABLE 2

Value of Chemical Shifts of $^1$H-NMR

| FGF inhibiting substance (400 MHz, DMSO-d$_6$, HCl) | | | | Complestatin (Reference 2) (400 MHz, DMSO-d$_6$) | | | |
|---|---|---|---|---|---|---|---|
| δ(ppm) | H | multiple | J(Hz) | δ(ppm) | H | multiple | J(Hz) |
| 10.94 | 1H | brs | | 10.9 | 1H | | |
| 10.85 | | br | | | | | |
| 9.85 | | br | | | | | |
| 9.02 | 1H | d | 7.32 | 8.863 | 1H | d | 6.8 |
| 8.74 | 1H | d | 5.79 | 8.741 | 1H | d | 6.2 |
| 8.56 | 1H | d | 6.10 | 8.507 | 1H | d | 6.3 |
| 8.29 | 1H | d | 9.46 | 8.285 | 1H | d | 9.2 |
| 7.93 | 1H | d | 7.63 | 7.877 | 1H | d | 7.8 |
| 7.82 | 1H | (dd) | 8.85 | 7.825 | 1H | dd | 2.0, 8.8 |
| 7.74 | 2H | s | | 7.776 | 2H | s | |
| 7.42 | 1H | d | 8.24 | 7.435 | 1H | d | 9.0 |
| 7.33 | 2H | s | | 7.341 | 2H | s | |
| 7.30 | 2H | s | | 7.305 | 2H | s | |
| 7.26 | 1H | d | 2.14 | 7.272 | 1H | d | 2.8 |
| 7.24 | 1H | s | | 7.249 | 1H | s | |
| 7.18 | 1H | (dd) | 8.24 | 7.192 | 1H | dd | 2.0, 8.6 |
| 7.10 | 2H | d | 8.54 | 7.109 | 2H | | 8.0 |
| 7.07 | 1H | (dd) | 2.74 | 7.079 | 1H | dd | 2.5, 7.0 |
| 6.85 | 1H | dd | 2.45, 8.55 | 6.867 | 1H | dd | 2.6, 8.2 |
| 6.82 | 1H | d | 9.46 | 6.830 | 1H | dd | 1.5, 8.2 |
| 6.77 | 2H | d | 8.55 | 6.765 | 2H | dd | 9.2 |
| 5.56 | 2H | d | 8.24 | 5.563 | 2H | | 8.4 |
| 5.46 | 1H | d | 2.44 | 5.475 | 1H | | 4.0 |
| 5.18 | 1H | d | 6.41 | 5.196 | 1H | | 7.0 |
| 5.09 | 1H | d | | 5.108 | 1H | | 3.5 |
| 5.05 | 2H | d | 6.1 | 5.065 | 2H | | 7.2 |
| 4.19 | 1H | ddd | | 4.182 | 1H | | |
| 3.42 | 1H | t | 13.12 | | | | |
| 3.04 | 1H | brs | | 3.050 | 1H | | |
| 2.97 | 3H | s | | 2.985 | 3H | | |
| 2.87 | 1H | d | 11.6 | 2.886 | 1H | | |

TABLE 3

Value of Chemical Shifts of $^{13}$C-NMR

| FGF inhibiting substance (100 MHz, DMSO-d$_6$, HCl) | Complestatin (Reference 2) (100 MHz, DMSO-d$_6$) | FGF inhibiting substance (100 MHz, DMSO-d$_6$, HCl) | Complestatin (Reference 2) (100 MHz, DMSO-d$_6$) |
|---|---|---|---|
| 186.28 | 185.7 | 126.88 | 127.0 |
| 171.30 | 171.3 | 126.67 | 126.7 |
| 170.25 | 170.3 | 126.26 | 126.4 |
| 169.81 | 169.8 | 126.18 | 126.3 |
| 169.17 | 169.2 | 125.59 | 124.1 |
| 168.40 | 168.4 | 123.63 | 123.7 |
| 167.52 | 167.6 | 123.54 | 123.6 |
| 163.63 | 163.7 | 123.09 | 123.1 |
| 157.15 | 157.1 | 122.22 | 122.5 |
| 155.16 | 155.8 | 121.96 | 122.0 |
| 154.34 | 155.2 | 121.63 | 121.7 |
| 149.51 | 149.6 | 121.58 | 118.4 |
| 148.66 | 148.7 | 118.31 | 115.3 |
| 148.13 | 148.1 | 115.27 | 114.4 |
| 139.34 | 139.4 | 114.34 | 111.5 |
| 136.19 | 136.3 | 111.38 | 110.5 |
| 134.38 | 134.5 | 110.43 | 61.3 |
| 134.26 | 134.4 | 61.17 | 57.1 |
| 131.88 | 131.9 | 57.03 | 55.8 |
| 131.44 | 131.5 | 55.72 | 55.2 |
| 131.04 | 131.1 | 55.18 | 55.0 |
| 130.93 | 131.0 | 54.93 | 51.5 |
| 130.49 | 130.6 | 51.40 | 35.0 |
| 129.99 | 130.1 | 35.03 | 31.2 |
| 129.43 | 129.5 | 31.19 | 28.2 |
| 128.11 | 128.2 | 28.11 | |
| 127.69 | 127.8 | | |

Example 3

Measurement of FGF Inhibitory Activity of Complestatin

FGF bonds to receptors on the surface of vascular endothelial cells and other cells, and promotes cell growth or migration. The FGF inhibitory activity of the complestatin obtained in the methods of Examples 1 and 2 was investigated using three methods. Basic fibroblast growth factor (bFGF) was used for the FGF.

1. Inhibitory Effect of Complestatin on Specific Binding to bFGF Receptors

The inhibitory effect of complestatin on specific binding to bFGF receptors was investigated in accordance with the method of A. Yayon, et al. used in Example 1, section 1(3) (Proc. Natl. Acad. Sci. USA, 90, 10643, 1993).

Here, binding medium containing various concentrations of complestatin was used for the sample solutions. Furthermore, binding medium not containing complestatin was used for the control sample solution and the same procedure as described above was performed on the control sample solution.

Figure 5:
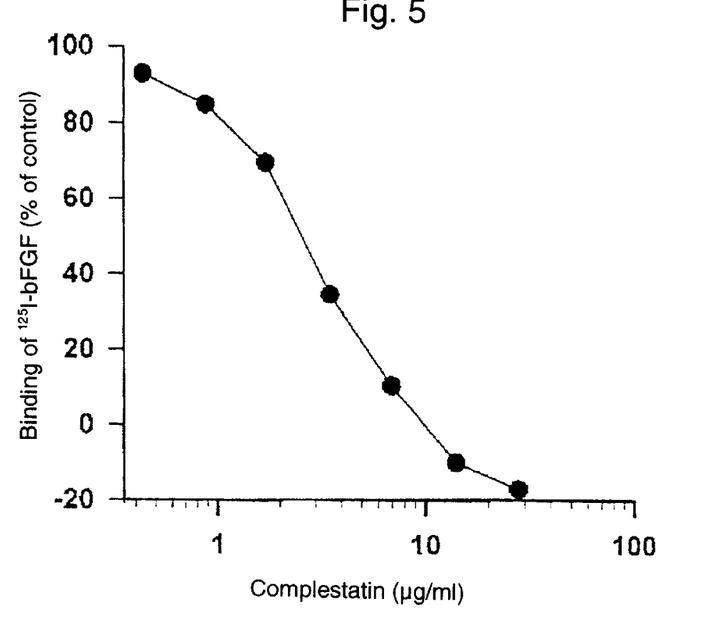
FIG. 5 is a graph showing the inhibitory effect of complestatin on specific binding of bFGF to receptors performed in Example 3, section 1.

The results are shown in FIG. 5. Complestatin was shown to concentration-dependently inhibit specific binding of $^{125}$I-bFGF to receptors, clearly indicating that complestatin has FGF inhibitory activity.

2. Inhibitory Effect of Complestatin on Cell Migration Stimulated by bFGF

The effect of complestatin on cell migration stimulated by bFGF was investigated using a 96-well chemotaxis chamber (available from NEURO PROBE CO.) installed with an 8 μm frame filter (available from NEURO PROBE CO.) precoated with gelatin.

Figure 6:
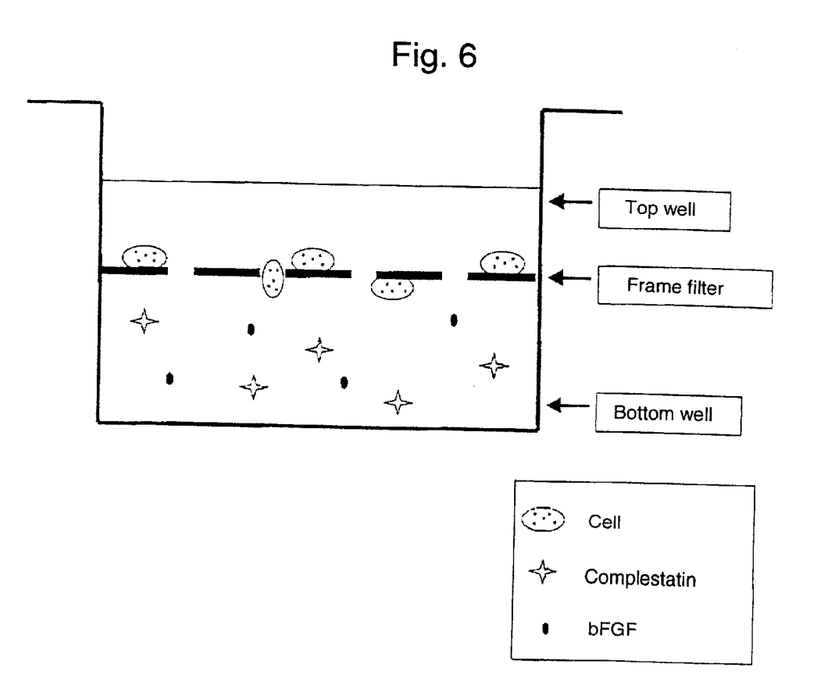
FIG. 6 is a schematic diagram of the experimental system used in Example 3, section 2.

The experimental principle is illustrated-in FIG. 6. When bFGF is placed in the bottom well, cells adhered to the frame filter in the top well migrate to the bottom well.

Addition of complestatin to the bottom well can be used to investigate the inhibitory effect of complestatin on cell movement.

(1) 100 μl of cell suspension (0.5% CS/DMEM containing Balb/3T3 clone A31 cells at a concentration of 5×10$^5$ cells/ml) were placed in the top wells. In addition, 35 μl of 0.5% CS/DMEM containing various concentrations of complestatin and 1 ng/ml of bFGF were placed in the bottom wells.

(2) After incubating the chamber for 5 hours at 37° C. in a $CO_2$ incubator, the frame filter was removed from the chamber, the cells were stained with Diff-Quik staining solution (trade name, available from Kokusai Shiyaku Co.), and the number of cells that migrated to the bottom surface of the filter was counted. Furthermore, with the exception of not adding complestatin to the bottom wells, the same procedure was performed for the control.

Figure 7:
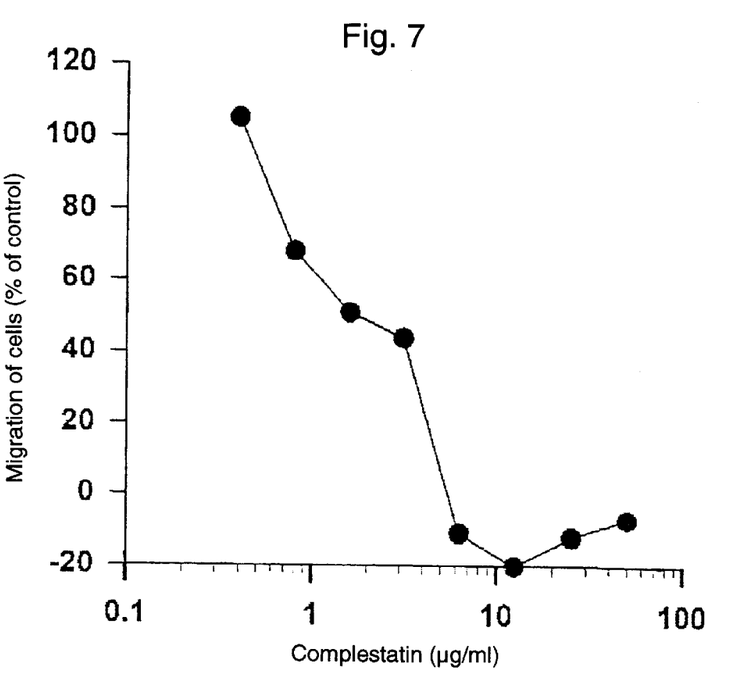
FIG. 7 is a graph showing the inhibitory effect of complestatin on the cell migration stimulated by bFGF performed in Example 3, section 2.

(3) The results are shown in FIG. 7. Complestatin was shown to concentration-dependently inhibit the Balb/3T3 clone A31 cell migration stimulated by bFGF. Complestatin was clearly shown to have FGF inhibitory activity.

3. Inhibitory Effect of Complestatin on Cell Growth Stimulated by bFGF

Growth of both fetal bovine heart endothelial (FBHE) cells and human umbilical vein endothelial cells (HUVEC) was promoted by addition of bFGF to the media. The inhibitory effect of complestatin on the cell growth stimulated by bFGF was investigated using these cells.

(1) 10% CS/DMEM containing FBHE at a concentration of $1 \times 10^4$ cells/ml was prepared for the cell suspension. One ml aliquots of this solution were then inoculated into each well of a 12-well plate and cultured for one day at 37° C. in a $CO_2$ incubator. 1 ng/ml of bFGF and various concentrations of complestatin were added to each well followed by additional culturing for 2 days at 37° C. in a $CO_2$ incubator. Next, the number of cells in each well was counted with a Coulter Counter (trade name, available from Coulter Electronics Co.).

(2) On the other hand, medium containing HUVEC at a concentration of $1 \times 10^4$ cells/ml (MCDB131 medium containing 10% fetal bovine serum, 25 mM HEPES (pH 7.5), 10 units/ml of penicillin and 10 $\mu$g/ml of streptomycin) was prepared for the cell suspension. One ml aliquots of the cell suspension were inoculated into each well of a 12-well plate precoated with type I collagen, and incubated for one day at 37° C. in a $CO_2$ incubator. 10 ng/ml of bFGF and various concentrations of complestatin were added to each well followed by additional incubation for 2 days at 37° C. in a $CO_2$ incubator. Next, the number of cells in each well was counted with a Coulter Counter (trade name, available from Coulter Electronics Co.). Furthermore, with the exception of not adding complestatin, the same procedure was performed for the control.

Figure 8:
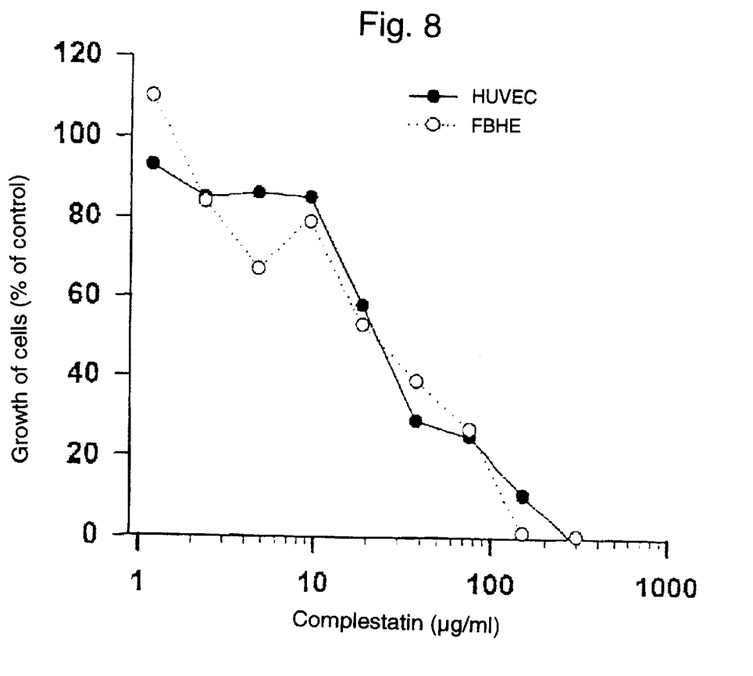
FIG. 8 is a graph showing the inhibitory effect of complestatin on the cell growth promotion activity of bFGF performed in Example 3, section 3.

(3) The results are shown in FIG. 8. Complestatin was shown to concentration-dependently inhibit growth of FBHE and HUVEC promoted by bFGF. Complestatin clearly has FGF inhibitory activity.

Example 4

Inhibitory Effect of Complestatin on Vascularization

The inhibitory effect of complestatin on angiogenesis was investigated using a modified method of Furubayashi, et al. (J. Jap. Pharm., 105, 357, 1995). In this method, vascular endothelial cells form a tube (blood vessel-like tubular structure) in collagen gel. Addition of complestatin to this system makes it possible to investigate the inhibitory effect of complestatin on angiogenesis.

(1) Collagen gel was prepared in the manner described below. To begin with, type I collagen solution (3 mg/ml, available from Wako Junyaku Co.), 10-fold concentrated HEPES-free DMEM, reconstitution buffer (2.2 g of sodium bicarbonate and 4.77 g of HEPES dissolved in 100 ml of 0.05 N aqueous sodium hydroxide solution) and deionized water were mixed on ice at a ratio of 5:1:1:3 followed by the addition of 0.75 ml aliquots to each well of a 12-well plate. This plate was then incubated for 20 minutes in an incubator at 37° C. to form a gel.

(2) A cell suspension was prepared by suspending $3 \times 10^5$ cells/ml of bovine aortic endothelial cells (BAEC) in 10% CS/DMEM, after which 1.5 ml aliquots were inoculated onto the collagen gel followed by culturing for one day at 37° C. in a $CO_2$ incubator. After removing the medium and washing four times with DMEM, 0.75 ml aliquots of the above-mentioned type I collagen solution were layered onto the plate followed by gelation at 37° C. in an incubator. 1.5 ml of 0.5% CS/DMEM containing various concentrations of complestatin were added to the resulting gel followed by culturing for 2 days at 37° C. in a $CO_2$ incubator.

(3) After culturing, photographs were taken of four fields randomly selected for each well and these photographs were then analyzed by using the Olympus image processing analyzer Type SP500F (trade name, available from Olympus Co.) to determine the lengths of all tubes. The length of tube was then divided by the field area to determine the tube length per unit area.

The tube formation inhibition rate of complestatin was calculated according to the following formula:

{1− (tube length per unit area at each concentration/tube length per unit area in the absence of addition of complestatin)}×100

The results are shown in Table 4.

TABLE 4

| Concentration of complestatin ($\mu$g/ml) | Tube formation inhibition rate (%) |
| --- | --- |
| 100 | 99 |
| 50 | 94 |
| 25 | 91 |
| 13 | 43 |
| 6.3 | 21 |
| 3.1 | 10 |
| 1.6 | 17 |
| 0.78 | 3 |

According to Table 4, it is clear that complestatin dose-dependently inhibits BAEC tube formation, namely that it has angiogenesis inhibitory activity. Based on the above, complestatin was shown to be useful as a angiogenesis inhibitor, and extremely useful as an agent for preventing, treating or improving various diseases involving FGF or angiogenesis.

Example 5

Inhibitory Effect of Complestatin on Vascularization in the Chick Embryo Choriallantoic Membrane The inhibitory effect of complestatin on angiogenesis in the chorioallantoic membrane of chick embryo was investigated according to the method of T. Oikawa, et al. (J. Antibiotics, 44, 1033, 1991). To begin with, a portion of the uppermost part of the air chamber measuring about 1 cm square was removed from three-day-old fertilized chicken eggs, and cultured for 2 days in a humidified incubator. A silicon ring having an outer diameter of 5 mm and inner diameter of 3 mm was placed on the 5-day-old chorioallantoic membrane, and 10 $\mu$l of a 1% methylcellulose solution containing various concentrations of the complestatin obtained in Example 2 were added to the inside of the ring.

Moreover, after incubating for 2 days, a suitable amount of fat emulsion (Intralipos, trade name, available from Midori Juji Co.) was injected beneath the chorioallantoic membrane to facilitate microscopic observation followed by observation of angiogenesis in the chorioallantoic membrane. Fertilized eggs in which a region free of blood vessels in the chorioallantoic membrane (having a diameter of at least 3 mm) were judged as having observed inhibition of angiogenesis by complestatin. Angiogenesis inhibition rate (%) was calculated according to the following formula:

100× (number of fertilized eggs in which inhibition of angiogenesis was observed)/(number of fertilized eggs used in test)

Those results are shown in Table 5.

TABLE 5

| Concentration of complestatin ($\mu$g/egg) | Angiogenesis inhibition rate (%) | Number of fertilized eggs used in test |
| --- | --- | --- |
| 0 | 0 | 21 |
| 6.25 | 14 | 29 |
| 12.5 | 33 | 21 |
| 25 | 33 | 21 |
| 50 | 52 | 27 |
| 100 | 77 | 26 |

According to Table 5, complestatin clearly exhibits concentration-dependent inhibition of angiogenesis in the chorioallantoic membrane.

Example 6

Measurement of Complestatin Antitumor Activity

The antitumor activity of complestatin was confirmed in an experiment using mouse fibrosarcoma (Meth A) cells. To begin with, $1\times10^6$ Meth A cells cultured in the abdominal cavity of BALB/c-nu/nu mice were transplanted subcutaneously to BALB/c-nu/nu mice (control group: 5 mice, experimental group: 5 mice), and tumor size was measured after 10 days.

Complestatin was dissolved in PBS, and administered intraperitoneally at 250$\mu$l/day once a day during days 1 to 4 and days 7 to 9. The dosing concentrations of complestatin were set at 5 mg/kg and 10 mg/kg. The tumor growth inhibition rate caused by complestatin was calculated according to the following formula:

{1− (tumor size at each dosing concentration/tumor size at dosing concentration of 0 mg/kg)}×100

Those results are shown in Table 6.

TABLE 6

| Concentration of complestatin administered | Growth inhibition rate (%) |
| --- | --- |
| 0 mg/kg | 0 |
| 5 mg/kg | 40 |
| 10 mg/kg | 68 |

According to Table 6, complestatin clearly demonstrated growth inhibitory action on tumor cells, and namely antitumor activity. Complestatin was shown to be useful as an antitumor agent.

Example 7

Measurement of Complestatin Antitumor Activity

The antitumor activity of complestatin was confirmed in an experiment using human leukemia (HL-60) cells. To begin with, $5\times10^6$ HL-60 cells were transplanted subcutaneously to CB17. SCID mice (control group: 4 mice, experimental group: 4 mice), and tumor size was measured after 20 days. Complestatin was dissolved in PBS, and administered intraperitoneally at 250$\mu$l/day once a day during days 1 to 3, days 5 to 9 and days 12 and 13. The dosing concentration of complestatin was set at 5 mg/kg. The tumor growth inhibition rate caused by complestatin was calculated according to the following formula:

{1− (tumor size at dosing concentration/tumor size at dosing concentration of 0 mg/kg)}×100

Those results are shown in Table 7.

TABLE 7

| Concentration of complestatin administered | Growth inhibition rate (%) |
| --- | --- |
| 0 mg/kg | 0 |
| 5 mg/kg | 76 |

According to Table 7, complestatin clearly demonstrated excellent antitumor activity.

Example 8

Preparation Example

| 1. Tablet Production | |
| --- | --- |
| Complestatin | 100 g |
| Lactose | 100 g |
| Cornstarch | 148.8 g |
| Magnesium stearate | 1.2 g |

The above powders were mixed and after passing through a 20 mesh sieve, filled into a No. 2 gelatin capsule to produce capsules containing 100 mg of complestatin per capsule.

| 2. Injection preparation production | |
| --- | --- |
| Complestatin | 5 g |
| Sodium chloride | 9 g |
| Chlorobutanol | 5 g |
| Sodium hydrogen carbonate | 1 g |

The above ingredients were dissolved in 1000 ml of distilled water and apportioned into ampoules to produce an injection preparation containing 5 mg of complestatin per 1 ampoule.

As has been described above, complestatin has been shown to have excellent FGF inhibitory activity, angiogenesis inhibitory activity and antitumor activity. FGF inhibitors, angiogenesis inhibitors and antitumor agents containing complestatins as an active ingredient can be used as drugs for the prevention, treatment and amelioration of various diseases involving FGF or angiogenesis (for example, inflammatory diseases, atherosclerosis, diabetic retinopathy and solid tumors), as well as various tumors not involving angiogenesis. In addition, the above inhibitors and agents are also extremely useful as reagents for research on FGF, angiogenesis or the above-mentioned diseases.

What we claimed is:

1. A method of treating diseases in which it is effective to inhibit FGF, and which are sensitive to complestatin comprising administering an effective amount of complestatin to a patient in need thereof.

2. The method of claim 1, wherein said diseases are diseases accompanying vascularization caused by FGF stimulation, tumors accompanying cell growth caused by FGF stimulation, or tumors accompanying abnormal expression of FGF.

3. The method of claim 2, wherein the tumors accompanying abnormal expression of FGF is brain tumors, lung cancer or kidney cancer.

4. The method of claim 3, wherein the tumor accompanying abnormal expression of FGF is lung cancer.

5. A method of treating diseases accompanying vascularization, and which are sensitive to complestatin comprising administering an effective amount of complestatin to a patient in need thereof.

6. The method of claim 5, wherein said diseases are inflammatory diseases, atherosclerosis, diabetic retinopathy or solid tumors.

7. The method of claim 6, wherein said diseases are rheumatism, rheumatoid arthritis, psoriasis, stomach cancer, colon cancer, lung cancer or pancreas cancer.

8. A method of treating diseases of tumors involving FGF, solid tumors involving angiogenesis, cancer of the blood, or ascites cancer, and which are sensitive to complestatin comprising administering an effective amount of complestatin to a patient in need thereof.

9. The method of claim 8, wherein said tumors involving FGF, solid tumors involving angiogenesis are stomach cancer, colon cancer, lung cancer or pancreas cancer.

10. The method of claim 8, wherein the complestatin is represented by the formula or its pharmacologically acceptable salts or esters.

11. A method of treating diseases in which it is effective to inhibit FGF, and which are sensitive to complestatin comprising administering an effective amount complestatin represented by the formula or its pharmacologically acceptable salts or esters to a patient in need thereof.

12. A method of treating diseases accompanying vascularization, and which are sensitive to complestatin comprising administering an effective amount of complestatin represented by the formula or its pharmacologically acceptable salts or esters to a patient in need thereof.

* * * * *